United States Patent [19]

Tanahashi et al.

[11] Patent Number: 5,783,601
[45] Date of Patent: Jul. 21, 1998

[54] EXTERNAL SKIN-CARE COMPOSITION

[75] Inventors: Masanori Tanahashi; Takahide Minami, both of Tokyo; Yukihiro Ohashi, Ichikai-machi; Shinya Amano, Ichikai-machi; Kouichi Niinaka, Ichikai-machi, all of Japan

[73] Assignee: Kao Corporation, Tokyo, Japan

[21] Appl. No.: 631,987

[22] Filed: Apr. 15, 1996

[30] Foreign Application Priority Data

Apr. 13, 1995 [JP] Japan ................... 7-088283

[51] Int. Cl.$^6$ ................... A61K 31/19
[52] U.S. Cl. ................... 514/557; 514/844; 514/847; 514/873
[58] Field of Search ................... 514/557, 844, 514/847, 873

[56] References Cited

U.S. PATENT DOCUMENTS 5,389,677  2/1995  Yu et al. ................... 514/557

OTHER PUBLICATIONS

Chemical Abstracts, vol. 125, AN–204139, JP-A–08 183 724, Jul. 16, 1996.

*Primary Examiner*—Shelley A. Dodson
*Assistant Examiner*—Michael A. Williamson
*Attorney, Agent, or Firm*—Oblon, Spivak, McClelland, Maier & Neustadt, P.C.

[57] ABSTRACT

Disclosed herein is an external skin-care composition comprising hydroxycarboxylic acids or derivatives thereof represented by the general formulae (1), (2), and (3), or the salts thereof:

$$CH_3CH(OH)(CH_2)_l COR^1 \quad (1)$$

$$CH_3CH_2CH(OH)(CH_2)_m COR^2 \quad (2)$$

$$CH_3CH_2CH_2CH(OH)(CH_2)_n COR^3 \quad (3)$$

wherein $R^1$, $R^2$, and $R^3$ are each independently a hydroxyl group, an amino group or an alkoxyl group which may be substituted by 1–3 hydroxyl groups, l is a number of 7–11, m is a number of 6–10, and n is a number of 5–9. This composition exhibits an excellent moisturizing effect, moisturizes the skin, has a great effect in preventing skin roughness and shows excellent effects in enhancing the clear skin tone of the skin and reducing skin dullness, and is hence particularly useful for cosmetic skin-care compositions.

20 Claims, No Drawings

EXTERNAL SKIN-CARE COMPOSITION

BACKGROUND OF THE INVENTION

1. Field of the Invention

The present invention relates to an external skin-care composition which has an excellent moisturizing effect, moisturizes the skin, can prevent skin roughness, enhances the clear skin tone of the skin and can reduce skin dullness.

2. Discussion of the Background

The water content of the horny layer has heretofore been known to be critical for imparting moisture to the skin to maintain the smoothness and softness of the skin. It has also been known that dirtiness of the skin, pigmentation, failure in blood circulation, and the like cause a worsening of the complexion, and that the clear skin tone of the skin is lost by lack of water in the horny layer and a disorder of a skin texture. Such skin dullness is not preferable from the viewpoint of beauty and hence becomes the target of care with cosmetic compositions.

The retention of water in the horny layer is said to rely upon a water-soluble component contained in the horny layer, namely, a free amino acid, organic acid, urea or inorganic ions. These materials have been incorporated either singly or in combination in medicinal external skin-care preparations or cosmetic compositions with a view toward improving or preventing skin roughness. Besides, many humectants having high affinity for water have also been developed and have been used for similar purposes. Further, beautifiers and cell activators have also been used for enhancing the clear skin tone of the skin.

However, these conventional humectants and beautifiers suffer from the drawbacks that their effects are temporary or insufficient, or it takes a long time to exhibit their effects. In addition, it has been attempted to cover the skin with powder to hide the color of the skin. However, the powder may remain as dirt in pores of the skin to form the cause of the skin dullness in some cases.

Thus, there remains a need for cosmetic compositions useful for moisturizing the skin, improving the clear skin tone of the skin, and reducing the dullness of the skin.

SUMMARY OF THE INVENTION

It is therefore an object of the present invention to provide novel external skin-care compositions which have an excellent ability to improve the water retention of the horny layer, can prevent skin roughness, enhances the clear skin tone of the skin, and can reduce skin dullness.

It is another object of the present invention to provide novel skin-care compositions which provide a long lasting improvement of skin roughness.

It is another object of the present invention to provide a method for improving or preventing skin roughness, improving the moisture content of the skin, enhancing the moisture retention of the horny layer, enhancing the clear skin tone of the skin, and reducing skin dullness.

In view of the foregoing circumstances, the present inventors have carried out various investigations as to external skin-care composition taking account of the ability to have water retained into the horny layer, the ability to exhibit such an effect, the duration of the effect, and the safety to the skin. As a result, it has been found that a mixture of three hydroxycarboxylic acids each having a specific structure has an excellent moisturizing effect, and an external skin-care composition, in which this mixture is incorporated, moisturizes the skin, can lastingly prevent skin roughness and shows great effects in enhancing the clear skin tone of the skin and improving skin dullness, thus leading to completion of the present invention.

According to the present invention, there is thus provided an external skin-care composition comprising a hydroxycarboxylic acid or a derivative thereof represented by the following general formula (1) or a salt thereof, a hydroxycarboxylic acid or a derivative thereof represented by the following general formula (2) or a salt thereof, and a hydroxycarboxylic acid or a derivative thereof represented by the following general formula (3) or a salt thereof:

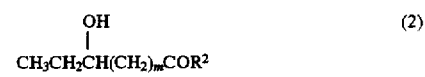

wherein $R^1$, $R^2$, and $R^3$ are each independently a hydroxyl group, an amino group, or an alkoxyl group which may be substituted by 1–3 hydroxyl groups, l is a number of 7–11, m is a number of 6–10, and n is a number of 5–9.

The external skin-care compositions according to the present invention exhibit an excellent moisturizing effect, moisturize the skin, have a great effect in preventing skin roughness, and show excellent effects in enhancing the clear skin tone of the skin and reducing skin dullness, and are hence particularly useful for cosmetic skin-care compositions.

DETAILED DESCRIPTION OF THE PREFERRED EMBODIMENTS

The external skin-care compositions according to the present invention are characterized in that the above three hydroxycarboxylic acids or the derivatives thereof (hereinafter referred to as the hydroxycarboxylic acids collectively), or salts thereof are incorporated therein. These hydroxycarboxylic acids or salts thereof may be separately available to incorporate them. It is however preferable to use a mixture of these three compounds, which is obtained in the course of their preparation. In the general formula (1), l is a number of 7–11, preferably 7–9, particularly preferably 8. In the general formula (2), m is a number of 6–10, preferably 6–8, particularly preferably 7. In the general formula (3), n is a number of 5–9, preferably 5–7, particularly preferably 6.

In the general formulae (1), (2), and (3), alkoxyl groups indicated by $R^1$, $R^2$, and $R^3$ include linear or branched alkoxyl groups having 1–24 carbon atoms, with linear or branched alkoxyl groups having 1–20 carbon atoms being particularly preferred. Specific examples of such alkoxyl groups include methoxy, ethoxy, n-propoxy, isopropoxy, n-butoxy, isobutyloxy, n-pentoxy, n-hexyloxy, 2-ethylhexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy and isooctadecyloxy groups. Examples of the alkoxyl groups substituted by at least one hydroxyl group include the above-mentioned alkoxyl groups substituted by 1–3 hydroxyl groups. Preferable examples thereof include hydroxyethyloxy and 2,3-dihydroxypropyloxy groups.

Examples of the salts of the hydroxycarboxylic acids (1), (2), and (3) include alkali metal salts such as the sodium and potassium salts; alkaline earth metal salts such as the calcium and magnesium salts; salts with amines such as amines and alkanolamines; salts with basic amino acids such as arginine and lysine; the guanidine salts; and sugar amino acid salts such as the glucosamine salts. Preferred salts are those of the compounds in which $R^1$, $R^2$, and $R^3$ are hydroxy. Thus, these salts have formulae (1), (2), and (3) in which $R^1$, $R^2$, and $R^3$ are $OR^4$, $OR^5$, and $OR^6$, respectively, in which $R^4$, $R^5{}_1$ and $R^6$ are one equivalent of a monocation discussed above (e.g., $Na^+$, $K^+$, $NH_4{}^+$, $(HOCH_2CH_2)_4N^+$, $ArgH^+$, $LysH^+$, etc) or one half of a dication discussed above ($Ca^{+2}$, $Mg^{+2}$, etc.).

No particular limitation is imposed on the compounding ratio between the hydroxycarboxylic acids (1), (2), and (3). However, the ratio (1):(2):(3) is preferably 60–95:4–35:1–5 by weight, with 70–85:10–25:2–4 by weight being particularly preferred.

The mixture of these three hydroxycarboxylic acids or the salts thereof can be prepared by adding formic acid to an olefin carboxylic acid and then hydrolyzing the resultant products in accordance with, for example, the following reaction scheme:

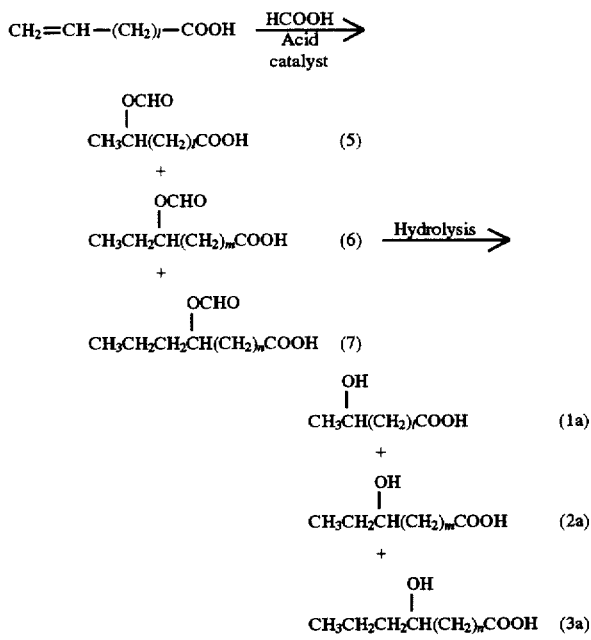

wherein l, m, and n have the same meanings as defined above.

Examples of the acid catalyst used in the reaction of the olefin carboxylic acid (4) with formic acid include sulfuric acid, perchloric acid, and a boron trifluoride-diethyl ether complex.

This reaction is preferably performed in the presence of 1–50 mol % of the acid catalyst at 20°–120° C., preferably 40°–80° C. for 0.1–48 hours using formic acid in a proportion of 1–30 moles per mole of the olefin carboxylic acid (4).

The hydrolysis of the resultant formyl esters (5), (6), and (7) is preferably performed under conventional conditions for the hydrolysis reaction, namely, under alkaline conditions such as potassium hydroxide or acidic conditions such as aqueous sulfuric acid.

The formyl esters (5), (6), and (7) can be converted to esters of their corresponding hydroxycarboxylic acids by reacting them with an alcohol in the presence of an acid catalyst. These esters can be then hydrolyzed to obtain hydroxycarboxylic acids (1a), (2a), and (3a). After formation of the esters of the hydroxycarboxylic acids, or the hydroxycarboxylic acids, these compounds can be further amidated in accordance with a method known per se in the art to derive their corresponding hydroxycarboxylic acid amides.

No particular limitation is imposed on the amount of the hydroxycarboxylic acids (1), (2), and (3) or the salts thereof to be incorporated into the external skin-care composition according to the present invention. In the case of an emulsion-type external skin-care composition, however, their amount is preferably 0.001–50 wt. % (hereinafter indicated merely by "%"), more preferably 0.01–20 wt. %, most preferably 0.1–10 wt. %, based on the total weight of the composition. In the case of an oil-based external skin-care composition containing a liquid hydrocarbon such as squalane as a base on the other hand, their amount is preferably 0.1–50 wt. %, more preferably 1–50 wt. %, most preferably 5–25 wt. %, based on the total weight of the composition. These amounts are for the total of the compounds of formulae (1), (2), and (3).

The external skin-care compositions according to the present invention may be classified roughly into medicinal external skin-care compositions and cosmetic skin-care compositions from the viewpoint of application. In these compositions, pharmaceutically permissible carriers or carriers permissible for cosmetics may be incorporated in addition to the hydroxycarboxylic acids (1), (2), and (3) or the salts thereof.

As examples of the medicinal external skin-care compositions, may be mentioned various ointments containing one or more medicinally-effective ingredients. The ointments include both those containing an oily base as a base and those containing an oil/water or water/oil emulsion-type base as a base. No particular limitation is imposed on the oily base. For example, vegetable oils, animal oils, synthetic oils, fatty acids, natural and synthetic glycerides, etc. may be mentioned. No particular limitation is also imposed on the medicinally-effective ingredients. For example, one or more of analgesic and antiphlogistic agents, antipruritics, disinfectants, astringents, emollients, hormones and the like may be used suitably as needed.

Where used as a cosmetic skin-care composition, it is possible to mix, in addition to the essential ingredients, those ingredients employed routinely as cosmetic ingredients such as oily substances, sterols, surfactants, water-soluble polyhydric alcohols, powders, silicones and the like in combination as needed.

No particular limitation is imposed on the oily substances used in the cosmetic skin-care compositions according to the present invention. As examples thereof, may be mentioned hydrocarbons such as solid and liquid paraffins, mineral oil, ceresin, ozocerite, montan wax, squalane and squalene; ester oils such as olive oil, carnauba wax, lanolin, jojoba oil, glyceryl monostearate, glyceryl distearate, glyceryl monooleate, isopropyl stearate, glycol neopentyl dicaprate and cholesterol isostearate; higher fatty acids such as stearic acid and palmitic acid; higher alcohol such as cetanol and stearyl alcohol; naturally extracted sphingosine derivatives; and synthetic sphingosine derivatives represented by the following general formula (8):

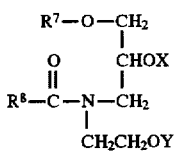

wherein $R^7$ is a linear or branched, saturated or unsaturated alkyl group having 10–26 carbon atoms, $R^8$ is a linear or branched, saturated or unsaturated alkyl group having 9–25 carbon atoms, and X and Y are independently a hydrogen atom or a sugar residue. These oily substances may be used either singly or in any combination thereof.

When these oily substances are incorporated, they may preferably be incorporated in a proportion of 0.001–50 wt. %, particularly preferably 0.005–30 wt. %, based on the total weight of the cosmetic skin-care composition.

As examples of the sterols incorporated in the cosmetic skin-care compositions according to the present invention, may be mentioned cholesterol, provitamin $D_3$, campesterol, stigmastanol, stigmasterol, 5-dihydrocholesterol, α-spinasterol, palysterol, clionasterol, γ-sitosterol, stigmasterol, sargasterol, avenasterol, ergostanol, sitosterol, corubisterol, chondrillasterol, poriferasterol, hliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, zymosterol, 7-hetocholesterol, lathosterol, 22-dehydrocholesterol, β-sitosterol, cholestatrien-3β-ol, coprostanol, cholestanol, ergosterol, 7-dehydrocholesterol, 24-dehydrocholestadien-3β-ol, equilenin, equilin, estrone, 17β-estradiol, androst-4-ene-3β,17β-diol, and dehydroepiandrosterone. These sterols may be used either singly or in any combination thereof.

When these sterols are incorporated, they may preferably be incorporated in a proportion of 0.001–50 wt. %, particularly preferably 0.005–30 wt. %, based on the total weight of the cosmetic skin-care composition.

As examples of the surfactants incorporated in the cosmetic skin-care compositions according to the present invention, may be mentioned polyoxyethylene alkyl ethers, polyoxyethylene fatty acid esters, polyoxyethylene sorbitan fatty acid esters, polyoxyethylene sorbitol fatty acid esters, glycerol fatty acid esters, polyoxyethylene hardened castor oil alkylsulfates, polyoxyethylene alkylsulfates, alkylphosphates, polyoxyethylene alkyl ether phosphates, alkali metal salts of fatty acids, sorbitan fatty acid esters, glycerol fatty acid esters and alkyl glyceryl ethers. These surfactants may be used either singly or in any combination thereof.

When these surfactants are incorporated, they may preferably be incorporated in a proportion of 0.001–50 wt. %, particularly preferably 0.005–30 wt. %, based on the total weight of the cosmetic skin-care composition.

As the water-soluble polyhydric alcohols incorporated in the cosmetic skin-care compositions according to the present invention, may be mentioned those having two or more hydroxyl groups in their molecules, for example, glycols such as ethylene glycol, propylene glycol, 1,3-propanediol, 1,3-butylene glycol, 1,4-butylene glycol, dipropylene glycol, isoprene glycol and hexylene glycol; glycol monoethers such as diethylene glycol monoethyl ether, diethylene glycol monobutyl ether, ethylene glycol monobutyl ether and ethylene glycol monoethyl ether; glycerol and polyglycerols such as diglycerol, triglycerol and tetraglycerol; glucose; maltose; maltitol; sucrose; fructose; xylitol; sorbitol; maltotriose; threitol; erythritol; and alcohols obtained by reduction of amylolytic sugar. These alcohols may be used either singly or in any combination thereof.

When these water-soluble polyhydric alcohols are incorporated, their proportion in the cosmetic skin-care composition may be suitably determined according to the preparation form of the composition. However, it is generally preferable to incorporate them in a proportion of 0.001–75 wt. %, particularly preferably 0.1–25 wt. %, based on the total weight of the cosmetic skin-care composition.

As examples of the powders incorporated in the cosmetic skin-care compositions according to the present invention, may be mentioned extenders such as mica, talc, sericite, kaolin, nylon powder and polymethylsilsesquioxane; inorganic pigments such as pearl; organic pigments such as Red Color No. 202, Red Color No. 226, Yellow Color No. 4 and aluminum lake; and inorganic powders for ultraviolet screening such as oil-absorbed powder, zinc oxide, titanium oxide, zirconium oxide and iron oxide. These powders may be subjected to a silicone treatment with methyl hydrogenmethylpolysiloxane, trimethylsiloxysilicic acid, methylpolysiloxane or the like, a fluorine treatment with a perfluoroalkyl phosphate, perfluoroalcohol or the like, an amino acid treatment with N-acylglutamic acid or the like, a lecithin treatment, a metal soap treatment, an alkylphosphate treatment, or the like before their use.

When these powders are incorporated, their proportion in the cosmetic skin-care composition may be suitably determined according to the preparation form of the composition. However, it is generally preferable to incorporate them in a proportion of 0.001–50 wt. %, particularly preferably 0.005–30 wt. %, based on the total weight of the cosmetic skin-care composition.

No particular limitation is imposed on the silicones incorporated in the cosmetic skin-care compositions according to the present invention. As examples thereof, may be mentioned octamethylpolysiloxane, tetradecamethylpolysiloxane, methylpolysiloxane, crosslinked methylpolysiloxane, high-polymeric methylpolysiloxane, and methylphenylpolysiloxane, and besides methylpolycyclosiloxanes such as octamethylcyclotetrasiloxane and decamethylcyclopentasiloxane, trimethylsiloxysilicic acid, and modified silicones such as polyether-alkyl-modified silicones, alkyl glyceryl ether-modified silicones.

When these silicones are incorporated, their proportion in the cosmetic skin-care composition may be suitably determined according to the preparation form of the composition. However, it is generally preferable to incorporate them in a proportion of 0.001–50 wt. %, particularly preferably 0.005–30 wt. %, based on the total weight of the cosmetic skin-care composition.

In the cosmetic skin-care compositions according to the present invention, various ingredients incorporated routinely in cosmetics, quasi-drugs, drugs and the like may also be incorporated within limits not impeding the object of the present invention. As examples of such ingredients, may be mentioned inorganic salts such as magnesium sulfate, potassium sulfate, sodium sulfate, magnesium chloride and sodium chloride; viscosity modifiers such as poly(vinyl alcohol), carboxyvinyl polymers, carboxymethylcellulose, gelatin, tragacanth gum, xanthan gum, hyaluronic acid, tuberose extract, agarose, and sodium alginate; and besides antiseptics such as parabens, pH adjustors, wetting agents, ultraviolet absorbents, coloring matter, medicinally-effective ingredients and perfume bases.

As the cosmetic skin-care compositions, cosmetic compositions of various forms may be formulated including, for example, water/oil type emulsified cosmetics, oil/water type emulsified cosmetics, creams, cosmetic emulsions, toilet waters, cosmetic jelly, oily cosmetics, lip sticks, foundations, packs, cleansings, body shampoos, scavengers, eye liner, mascara, etc. These compositions may be formulated by conventional techniques known to those skilled in the art.

In another embodiment, the present invention provides a novel method for treating and/or preventing skin roughness by applying the present cosmetic skin-care composition to the skin. Typically, the cosmetic skin-care composition of the present invention is applied in such an amount that 1 to 200 µg/cm$^2$, preferably 1 to 150 µg/cm$^2$, of the compounds of formulae (1), (2), and (3) (in total) are applied per 1 cm$^2$ of the skin. The present method is usually carried out by applying the present composition to the face, but the composition may also be applied to the hands, elbows, knees, feet, etc. Typically, the composition is applied once or twice per day, e.g., in the morning and evening.

Other features of the invention will become apparent in the course of the following descriptions of exemplary embodiments which are given for illustration of the invention and are not intended to be limiting thereof.

EXAMPLES

Unless otherwise indicated all amounts given in "%" are in terms of wt. % based on the total weight of the composition. The terms "bal" and "balance" mean that that ingredient is present in the composition in such an amount to make the total amount of all ingredients in the composition equal 100 wt. %.

SYNTHESIS EXAMPLE 1:

Synthesis of a mixture of 10-hydroxyundecanoic acid, 9-hydroxyundecanoic acid and 8-hydroxyundecanoic acid:

A 2-liter flask was charged with 400 g (2.17 mol) of undecylic acid, 1020 g (21.7 mol) of formic acid and 21.3 g (0.217 mol) of sulfuric acid. The contents were heated and stirred at 60° C. for 5 hours. The reaction mixture was washed with water and 25% saline and then distilled under reduced pressure, thereby obtaining 311.9 g (yield: 71.6%) of a mixture of 10-, 9-, and 8-formyloxyundecanoic acids.

A 2-liter flask was then charged with 300 g (1.30 mol) of the mixture, to which an aqueous solution of sodium hydroxide (NaOH: 156.2 g; water: 600 g) was added, followed by stirring at room temperature for 12 hours. After neutralizing the reaction mixture with sulfuric acid, it was extracted with dichloromethane. The resultant extract was washed with 5% saline. The solvent was distilled off under reduced pressure, thereby obtaining 255.2 g (yield: 96.9%) of a mixture of 10-, 9-, and 8-hydroxyundecanoic acids. Its capillary GC analysis revealed that the ratio between 10-hydroxyundecanoic acid, 9-hydroxyundecanoic acid, and 8-hydroxyundecanoic acid in the mixture was 82.1:15.4:2.5 by weight.

Example 1:

A mixture, which had been formulated by mixing the hydroxycarboxylic acid mixture obtained in Synthesis Example 1 and vaseline in a weight ratio of 1:3, was evaluated for skin conductance and skin roughness by the following respective methods. The results are shown in Table 2.

(Testing methods)

Chosen as volunteers in winter were 10 women of 20–50 years of age who had skin roughness on both of their cheeks. Different external skin-care preparations were applied separately to the left and right cheeks of each volunteer for 2 weeks. On the following day of the completion of the two-week application test, tests were conducted with respect to the following properties.

(1) Skin conductance:

After washing the face with warm water at 37° C., each volunteer was allowed to rest for 20 minutes in a room which was air-conditioned at 20° C. and 40% humidity. The water content of her horny layer was measured by a skin conductance meter (manufactured by IBS Company). A smaller conductance value indicates greater skin roughness. Conductance values of 5 and smaller indicate severe skin roughness. On the contrary, no substantial skin roughness is observed where this value is 20 or greater.

(2) Score of skin roughness:

Skin roughness was observed visually and ranked in accordance with the following standard shown in Table 1. Each score was indicated by an average value.

TABLE 1

| Score | Ranking of skin roughness |
| --- | --- |
| 0 | No skin roughness was observed. |
| 1 | Slight skin roughness was observed. |
| 2 | Skin roughness was observed. |
| 3 | Rather severe skin roughness was observed. |
| 4 | Severe skin roughness was observed. |

TABLE 2

|  | Skin conductance | Score of skin roughness |
| --- | --- | --- |
| Hydroxycarboxylic acid mixture | 35 | 0.3 |
| Control*[1] | 6 | 2.4 |

*: The comparative product used as a control contained only vaseline.

Example 2:

Using the hydroxycarboxylic acid mixture obtained in Synthesis Example 1, external skin-care compositions (emulsified cosmetic compositions) of their corresponding compositions shown below in Table 3 were formulated. Their effects for the improvement of skin roughness were evaluated in the same manner as in Example 1. The results are also shown collectively in Table 3.

TABLE 3

|  | Invention product | | | Comparative product | | |
| --- | --- | --- | --- | --- | --- | --- |
|  | 1 | 2 | 3 | 1 | 2 | 3 |
| Isostearyl glyceryl ether | 2.0 | — | — | 2.0 | — | — |
| Arginine moncetyl-phosphate | — | 2.0 | — | — | 2.0 | — |
| Polyoxyethylene (20) sorbitan stearate | — | — | 1.0 | — | — | 1.0 |
| Sorbitan monstearate | — | — | 1.0 | — | — | 1.0 |
| 2-Octyldodecyl myristate | 10.0 | 10.0 | 10.0 | 10.0 | 10.0 | 10.0 |
| Vaseline | 3.0 | 3.0 | 3.0 | 3.0 | 3.0 | 3.0 |
| Squalane | 5.0 | 5.0 | 5.0 | 5.0 | 5.0 | 5.0 |
| Tocopherol acetate | 0.5 | 0.5 | 0.5 | 0.5 | 0.5 | 0.5 |
| Hydroxycarboxylic acid mixture | 1.0 | 1.0 | 1.0 | — | — | — |
| Water | Bal | Bal | Bal | Bal | Bal | Bal |
| Score of skin roughness | 0.6 | 0.8 | 0.9 | 2.0 | 2.5 | 2.8 |

As is apparent from Examples 1 and 2, the external skin-care compositions according to the present invention, in which the hydroxycarboxylic acid mixture was incorporated, exhibited excellent moisturizing effects and skin roughness-preventing effects.

Example 3:

With respect to external skin-care compositions according to the present invention, their effects for the improvement of the transparency of the skin were investigated in the following manner.

(Evaluating method)

A green skin of a pig was cut into pieces about 5 cm square, and these pieces were immersed in hot water of 60°–65° C. and then cooled with water. The epidermis was separated from the pieces of skin by means of a spurtle. The thus-obtained epidermis was immersed in a 0.5% solution of trypsin to remove epidermic cell, thereby obtaining horny layer sheets. The thus-obtained horny layer sheets were cut into sheets 2 cm square. The thus-cut horny layer sheets were separately coated with Invention Products 4 to 16 and Comparative Products 4 to 18. After 30 minutes, excess composition was rubbed out of the horny layer sheets with paper. Each of the thus-treated sheets was fixed on a black mount. The degree that the black color of the mount was seen through the horny layer sheet was determined with a camera. Supposing a luminance of a certain darkness or lower is black, the area (hereinafter referred to as "black area"), which was regarded as black through the horny layer sheet, was determined by an image analysis system, thereby evaluating the transparency of the horny layer sheet. The transparency value of each test composition was determined in accordance with the following equation in which the transparency values of the comparative product 4 and the mount, on which no horny layer sheet was placed, are 0 and 100, respectively. (When transparency is high, the black color can be fully seen, and so the transparency value approaches 100)

Transparency (%) =

$$\frac{\left(\begin{array}{c}\text{Black area when coated}\\\text{with each test product}\end{array}\right) - \left(\begin{array}{c}\text{Black area when coated}\\\text{with Comp. Product 4}\end{array}\right)}{\text{Black area of the mount itself}} \times 100$$

The effect for the improvement of transparency of the skin was ranked in accordance with the following standard:

A: Transparency higher than 20% (transparency was markedly improved as compared with the control);

B: Transparency ranging from 5% to 20% (transparency was comparatively improved as compared with the control);

C: Transparency higher than 0% but lower than 5% (transparency was slightly improved as compared with the control); and D: Transparency not higher than 0% (transparency was not improved as compared with the control).

As apparent from Tables 4 to 7 shown below, it is understood that the external skin-care compositions according to the present invention are excellent in the effect of improving the transparency or clear skin tone of the skin.

TABLE 5

| | Invention product | | |
|---|---|---|---|
| Component (%) | 11 | 12 | 13 |
| Arginine 10-hydroxyundecanoate | 4.00 | — | 1.00 |
| Arginine 9-hydroxyundecanoate | 0.85 | 0.10 | — |
| Arginine 8-hydroxyundecanoate | 0.15 | 0.10 | — |
| Potassium 10-hydroxyundecanoate | — | 1.00 | — |
| Potassium 9-hydroxyundecanoate | — | 0.25 | — |
| Potassium 8-hydroxyundecanoate | — | — | 0.05 |
| Glyceryl 10-hydroxyundecanoate | — | 2.00 | — |
| Glyceryl 9-hydroxyundecanoate | — | — | 0.50 |
| Glyceryl 8-hydroxyundecanoate | — | — | 0.05 |
| Ethyl 10-hydroxyundecanoate | — | — | 1.00 |
| Ethyl 9-hydroxyundecanoate | — | 1.00 | — |
| Ethyl 8-hydroxyundecanoate | — | — | 0.05 |
| 10-Hydroxyundecanoic acid | — | 0.50 | 2.00 |
| 9-Hydroxyundecanoic acid | — | — | 0.35 |
| 8-Hydroxyundecanoic acid | — | 0.05 | — |
| Polyoxyethylene hardened castor oil (60 EO) | 1.0 | 1.0 | 1.0 |
| Ethanol | 10.0 | 10.0 | 10.0 |
| Antiseptic | q.s. | q.s. | q.s. |
| Purified water | Balance | Balance | Balance |
| Degree of improvement in transparency | A | A | A |

TABLE 6

| | Invention product | | |
|---|---|---|---|
| Component (%) | 14 | 15 | 16 |
| 8-Hydroxynonanoic acid | — | 2.00 | — |
| 7-Hydroxynonanoic acid | — | 0.45 | — |
| 6-Hydroxynonanoic acid | — | 0.10 | — |
| 9-Hydroxydecanoic acid | 2.00 | — | — |
| 8-Hydroxydecanoic acid | 0.45 | — | — |
| 7-Hydroxydecanoic acid | 0.10 | — | — |
| 11-Hydroxydodecanoic acid | 2.00 | — | — |
| 10-Hydroxydodecanoic acid | 0.40 | — | — |
| 9-Hydroxydodecanoic acid | 0.05 | — | — |
| 12-Hydroxytridecanoic acid | — | — | 2.00 |
| 11-Hydroxytridecanoic acid | — | — | 0.45 |
| 10-Hydroxytridecanoic acid | — | — | 0.10 |
| 13-Hydroxytetradecanoic acid | — | 2.00 | 2.00 |
| 12-Hydroxytetradecanoic acid | — | 0.45 | 0.40 |
| 11-Hydroxytetradecanoic acid | — | 0.10 | 0.05 |
| Polyoxyethylene hardened castor oil (60 EO) | 1.0 | 1.0 | 1.0 |
| Ethanol | 10.0 | 10.0 | 10.0 |

TABLE 4

| | Invention product | | | | | | | Comparative product | | | |
|---|---|---|---|---|---|---|---|---|---|---|---|
| Component (%) | 4 | 5 | 6 | 7 | 8 | 9 | 10 | 4 | 5 | 6 | 7 |
| 10-Hydroxyundecanoic acid | 3.00 | 4.00 | 4.75 | 2.50 | 2.50 | 4.00 | 4.90 | — | 5.00 | — | — |
| 9-Hydroxyundecanoic acid | 1.75 | 0.85 | 0.20 | 2.25 | 0.50 | 0.25 | 0.05 | — | — | 5.00 | — |
| 8-Hydroxyundecanoic acid | 0.25 | 0.15 | 0.05 | 0.25 | 2.00 | 0.75 | 0.05 | — | — | — | 5.00 |
| Polyoxyethylene hardened castor oil (60 EO) | 1.0 | 1.0 | 1.0 | 1.0 | 1.0 | 1.0 | 1.0 | 1.0 | 1.0 | 1.0 | 1.0 |
| Ethanol | 10.0 | 10.0 | 10.0 | 10.0 | 10.0 | 10.0 | 10.0 | 10.0 | 10.0 | 10.0 | 10.0 |
| Antiseptic | q.s. | q.s. | q.s. | q.s. | q.s. | q.s. | q.s. | q.s. | q.s. | q.s. | q.s. |
| Purified Water | Bal | Bal | Bal | Bal | Bal | Bal | Bal | Bal | Bal | Bal | Bal |
| Degree of improvement in transparency | A | A | A | B | B | B | B | D | C | C | C |

TABLE 6-continued

| | Invention product | | |
|---|---|---|---|
| Component (%) | 14 | 15 | 16 |
| Antiseptic | q.s. | q.s. | q.s. |
| Purified water | Balance | Balance | Balance |
| Degree of improvement in transparency | A | B | B |

30 minutes, 6 competent judges compared the right face of each volunteer with the left face, whereby the improvement was ranked by the number of women who were judged to exhibit a clear skin tone for the skin on the test sample-coated side superior to that on the contrast-coated side (an average of the 6 judges).

As apparent from the results shown below in Table 8, the external skin-care compositions according to the present invention comprising the respective hydroxycarboxylic acid mixtures were excellent in the effects of enhancing a clear skin tone of the human skin and reducing skin dullness.

TABLE 7

| | Comparative product | | | | | | | | | | |
|---|---|---|---|---|---|---|---|---|---|---|---|
| Component (%) | 8 | 9 | 10 | 11 | 12 | 13 | 14 | 15 | 16 | 17 | 18 |
| Squalane | 5.00 | — | — | — | — | — | — | — | — | — | — |
| Triolein | — | 5.00 | — | — | — | — | — | — | — | — | — |
| Silicone oil [KF96A (6cS), product of Shin-Etsu Chemical Co., Ltd. | — | — | 5.00 | — | — | — | — | — | — | — | — |
| Liquid paraffin | — | — | — | 5.00 | — | — | — | — | — | — | — |
| Isostearyl alcohol | — | — | — | — | 5.00 | — | — | — | — | — | — |
| Isostearic acid | — | — | — | — | — | 5.00 | — | — | — | — | — |
| 1,3-Butylene glycol | — | — | — | — | — | — | 5.00 | — | — | — | — |
| Glycerol | — | — | — | — | — | — | — | 5.00 | — | — | — |
| Dipropylene glycol | — | — | — | — | — | — | — | — | 5.00 | — | — |
| Polyethylene glycol 1500 | — | — | — | — | — | — | — | — | — | 5.00 | — |
| Sorbitol | — | — | — | — | — | — | — | — | — | — | 5.00 |
| Polyoxyethylene hardened castor oil (60 EO) | 1.0 | 1.0 | 1.0 | 1.0 | 1.0 | 1.0 | 1.0 | 1.0 | 1.0 | 1.0 | 1.0 |
| Ethanol | 10.0 | 10.0 | 10.0 | 10.0 | 10.0 | 10.0 | 10.0 | 10.0 | 10.0 | 10.0 | 10.0 |
| Antiseptic | q.s. | q.s. | q.s. | q.s. | q.s. | q.s. | q.s. | q.s. | q.s. | q.s. | q.s. |
| Purified water | Bal | Bal | Bal | Bal | Bal | Bal | Bal | Bal | Bal | Bal | Bal |
| Degree of improvement in transparency | C | C | C | C | C | C | C | C | C | C | C |

Example 4:

The external skin-care compositions according to the present invention were evaluated as to the effect for the improvement of the clear skin tone of the skin by actually applying them to human skin.

(Evaluating method)

Each of Inventive Products 4 to 6 and Comparative Products 4 to 8 was applied to one half of the face of fifteen women (22–31 years of age) as volunteers, while Comparative Product 4 was applied as control to the other half. After

TABLE 8

| | Invention product | | | Comparative product | | | | |
|---|---|---|---|---|---|---|---|---|
| Component (%) | 4 | 5 | 6 | 4 | 5 | 6 | 7 | 8 |
| 10-Hydroxyundecanoic acid | 3.00 | 4.00 | 4.75 | — | 5.00 | — | — | — |
| 9-Hydroxyundecanoic acid | 1.75 | 0.85 | 0.20 | — | — | 5.00 | — | — |
| 8-Hydroxyundecanoic acid | 0.25 | 0.15 | 0.05 | — | — | — | 5.00 | — |
| Squalane | — | — | — | — | — | — | — | 5.00 |
| Polyoxyethylene hardened castor oil (60 EO) | 1.0 | 1.0 | 1.0 | 1.0 | 1.0 | 1.0 | 1.0 | 1.0 |
| Ethanol | 10.0 | 10.0 | 10.0 | 10.0 | 10.0 | 10.0 | 10.0 | 10.0 |
| Antiseptic | q.s. | q.s. | q.s. | q.s. | q.s. | q.s. | q.s. | q.s. |
| Purified water | Balance | Balance | Balance | Balance | Balance | Balance | Balance | Balance |
| Number of women who were judged to show enhancement of a transparent feeling toward the skin | 12.1 | 13.1 | 12.4 | 0.17 | 4.4 | 5.6 | 4.2 | 3.3 |

Example 5: (Toner)

A toilet water was prepared in accordance with the following formulation.

| | (%) |
|---|---|
| 10-Hydroxyundecanoic acid | 0.75 |
| 9-Hydroxyundecanoic acid | 0.20 |
| 8-Hydroxyundecanoic acid | 0.05 |
| Arginine | 0.4 |
| Lysine | 0.4 |
| Polyoxyethylene hardened castor oil (40 EO) | 1.5 |
| Methylpolysiloxane.methyl (polyoxyethylene)-siloxane copolymer (SH3775C, product of Dow Corning Toray Silicone Co., Ltd.) | 0.6 |
| Glycerol | 5.0 |
| 1,3-Butylene glycol | 3.0 |
| Glycinebetaine | 0.2 |
| Trisodium citrate | 0.9 |
| Citric acid | 0.4 |
| Urea | 0.5 |
| ε-Aminocaproic acid | 0.1 |
| Ethanol | 5.0 |
| Antiseptic | q.s. |
| Perfume base | q.s. |
| Purified water | Balance |
| Total | 100 |

Example 6: (Toner)

A toilet water was prepared in accordance with the following formulation.

| | (%) |
|---|---|
| 10-Hydroxyundecanoic acid | 0.89 |
| 9-Hydroxyundecanoic acid | 0.20 |
| 8-Hydroxyundecanoic acid | 0.02 |
| Triethanolamine | 0.4 |
| Potassium hydroxide | 0.2 |
| Polyoxyethylene isocetyl ether (20 EO) | 0.3 |
| Sodium polyoxyethylene oleyl ether phosphate (8 EO) | 0.3 |
| Sodium polyoxyethylene dialkylphosphate (10 EO) | 0.1 |
| Polyethylene glycol 1500 | 2.0 |
| Polyoxyethylene methylglucoside (10 EO) | 1.5 |
| Dipropylene glycol | 0.5 |
| Disodium hydrogenphosphate | 0.5 |
| Succinic acid | 0.3 |
| Ethanol | 10.0 |
| Royal jelly extract | 2.0 |
| Antiseptic | q.s. |
| Perfume base | q.s. |
| Purified water | Balance |
| Total | 100 |

Example 7: (Cosmetic jelly)

A cosmetic jelly was prepared in accordance with the following formulation.

| | (%) |
|---|---|
| 10-Hydroxyundecanoic acid | 1.7 |
| 9-Hydroxyundecanoic acid | 0.2 |
| 8-Hydroxyundecanoic acid | 0.1 |
| Polyoxyethylene isocetyl ether (20 EO) | 1.0 |
| Sodium polyoxyethylene trialkylphosphate (10 EO) | 1.0 |
| Sorbitol | 0.5 |
| 1,3-Propanediol | 0.5 |
| Xanthan gum | 0.5 |
| Tuberose polysaccharide | 3.0 |
| Carboxyvinyl polymer (Carbopol 940, product of Goodrich Company) | 0.2 |
| Dipotassium glycyrrhetinate | 0.1 |
| Potassium hydroxide | 0.9 |
| Allantoin | 0.1 |
| Tannic acid | 0.2 |
| Ethanol | 20.0 |
| Antiseptic | q.s. |
| Perfume base | q.s. |
| Purified water | Balance |
| Total | 100 |

Example 8: (Cosmetic jelly)

A cosmetic jelly was prepared in accordance with the following formulation.

| | (%) |
|---|---|
| 10-Hydroxyundecanoic acid | 1.5 |
| 9-Hydroxyundecanoic acid | 0.4 |
| 8-Hydroxyundecanoic acid | 0.1 |
| Silicone composition (KSG-17, product of Shin-Etsu Chemical Co., Ltd.) | 5.0 |
| Methylpolysiloxane [KF96A-6cs, product of Shin-Etsu Chemical Co., Ltd.) | 15.0 |
| Metliylpolysiloxane (SH244, product of Dow Corning Toray Silicone Co., Ltd.) | 5.0 |
| Methylpolysiloxane.methyl (polyoxyethylene)-siloxane copolymer (SH3771C, product of Dow Corning Toray Silicone Co., Ltd.) | 2.0 |
| Methylpolysiloxane.methyl (polyoxyethylene)-siloxane copolymer (SH3775C, product of Dow Corning Toray Silicone Co., Ltd.) | 1.0 |
| Hydroxyethylcellulose hydroxypropyltrimethyl-ammonium chloride ether (Caticello H-60, product of Kao Corporation) | 0.02 |
| dl-α-Tocopherol acetate | 0.05 |
| Isostearyl glycyrrhetinate | 0.1 |
| Isopropylmethylphenol | 0.1 |
| EDTA | 0.1 |
| Ethanol | 5.0 |
| Antiseptic | q.s. |
| Perfume base | q.s. |
| Purified water | Balance |
| Total | 100 |

Example 9: (Cosmetic emulsion)

A cosmetic emulsion was prepared in accordance with the following formulation.

| | (%) |
|---|---|
| 10-Hydroxyundecanoic acid | 1.07 |
| 9-Hydroxyundecanoic acid | 0.36 |
| 8-Hydroxyundecanoic acid | 0.07 |
| N-(3-hexadecyloxy-2-hydroxypropyl)-N-2-hydroxyethyldecanamide | 0.5 |
| N-(3-hexadecyloxy-2-hydroxypropyl)-N-2-hydroxyethylhexadecanamide | 1.0 |
| N-(3-tetradecyloxy-2-hydroxypropyl)-N-2-hydroxyethyldecanamide | 0.5 |
| Polyoxyethylene hardened castor oil (10 EO) | 1.0 |
| Methylpolysiloxane.methyl (polyoxyethylene)-siloxane copolymer (SH3775C, product of Dow Corning Toray Silicone Co., Ltd.) | 1.0 |
| Sorbitan monostearate | 0.2 |
| Sodium stearoylmethyltaurine | 0.5 |
| Cholesterol | 0.8 |
| Cholesterol isostearate | 0.2 |
| Monocholesteryl alkenylsuccinate | 0.8 |

-continued

|  | (%) |
|---|---|
| Stearic acid | 0.2 |
| Palmitic acid | 0.3 |
| Myristic acid | 0.1 |
| Glycol pentyl dicaprate | 4.0 |
| Methylpolysiloxane [KF96A-500cs, product of Shin-Etsu Chemical Co., Ltd.) | 2.0 |
| Isostearyl alcohol | 1.2 |
| Cetyl alcohol | 1.0 |
| Glycerol | 3.5 |
| Lactic acid | 0.2 |
| Sodium lactate | 0.3 |
| Antiseptic | q.s. |
| Perfume base | q.s. |
| Purified water | Balance |
| Total | 100 |

Example 10: (Toner)

A toilet water was prepared in accordance with the following formulation.

|  | (%) |
|---|---|
| 7-Hydroxyoctanoic acid | 0.75 |
| 7-Hydroxynonanoic acid | 0.20 |
| 7-Hydroxydecanoic acid | 0.05 |
| Arginine | 0.4 |
| Lysine | 0.4 |
| Polyoxyethylene hardened castor oil (40 EO) | 1.5 |
| Methylpolysiloxane.methyl (polyoxyethylene)-siloxane copolymer (SH3775C, product of Dow Corning Toray Silicone Co., Ltd.) | 0.6 |
| Maltitol | 5.0 |
| Ethylene glycol monoethyl ether | 0.2 |
| Trisodium citrate | 0.9 |
| Citric acid | 0.4 |
| Urea | 0.5 |
| ε-Aminocaproic acid | 0.1 |
| Ethanol | 5.0 |
| Antiseptic | q.s. |
| Perfume base | q.s. |
| Purified water | Balance |
| Total | 100 |

Example 11: (Toner)

A toilet water was prepared in accordance with the following formulation.

|  | (%) |
|---|---|
| 11-Hydroxydodecanoic acid | 0.73 |
| 11-Hydroxytridecanoic acid | 0.32 |
| 11-Hydroxytetradecanoic acid | 0.03 |
| Diisopropanolamine | 0.4 |
| Potassium hydroxide | 0.2 |
| Polyoxyethylene isocetyl ether (20 EO) | 0.3 |
| Sodium polyoxyethylene oleyl ether phosphate (8 EO) | 0.3 |
| Sodium polyoxyethylene dialkylphosphate (10 EO) | 0.1 |
| Polyethylene glycol 1500 | 2.0 |
| Polyoxyethylene methylglucoside (20 EO) | 1.5 |
| Isoprene glycol | 0.5 |
| Disodium hydrogenphosphate | 0.5 |
| Succinic acid | 0.3 |
| Ethanol | 10.0 |
| Yeast extract | 2.0 |
| Antiseptic | q.s. |
| Perfume base | q.s. |
| Purified water | Balance |
| Total | 100 |

Example 12: (Cosmetic jelly)

A cosmetic jelly was prepared in accordance with the following formulation.

|  | (%) |
|---|---|
| Ethyl 10-hydroxyundecanoate | 1.7 |
| Glyceryl 9-hydroxyundecanoate | 0.2 |
| Hydroxyethyl 8-hydroxyundecanoate | 0.1 |
| Polyoxyethylene isocetyl ether (20 EO) | 1.0 |
| Sodium polyoxyethylene trialkylphosphate (10 EC) | 1.0 |
| Sorbitol | 0.5 |
| 1,3-Propanediol | 0.5 |
| Xanthan gum | 0.5 |
| Tuberose polysaccharide | 3.0 |
| Carboxyvinyl polymer (Carbopol 940, product of Goodrich Company) | 0.2 |
| Potassium hydroxide | 0.9 |
| Allantoin | 0.1 |
| Zinc sulfocarbolate | 0.2 |
| Ethanol | 20.0 |
| Antiseptic | q.s. |
| Perfume base | q.s. |
| Purified water | Balance |
| Total | 100 |

Example 13: (Cosmetic jelly)

A cosmetic jelly was prepared in accordance with the following formulation.

|  | (%) |
|---|---|
| Isopropyl 9-hydroxydecanoate | 1.5 |
| Glycine 8-hydroxydecanoate | 0.4 |
| Ethyl 9-hydroxydodecanoate | 0.1 |
| Silicone composition (KSG-16, product of Shin-Etsu Chemical Co., Ltd.) | 5.0 |
| Methylpolysiloxane [KF96A-6cs, product of Shin-Etsu Chemical Co., Ltd.) | 15.0 |
| Methylpolysiloxane (SH244, product of Dow Corning Toray Silicone Co., Ltd.) | 5.0 |
| Methylpolysiloxane.methyl (polyoxyethylene)-siloxane copolymer (SH3771C, product of Dow Corning Toray Silicone Co., Ltd.) | 2.0 |
| Methylpolysiloxane.methyl (polyoxyethylene)-siloxane copolymer (SH3775C, product of Dow Corning Toray Silicone Co., Ltd.) | 1.0 |
| Hydroxyethylcellulose hydroxypropyltrimethyl-ammonium chloride ether (Caticello H-60, product of Kao Corporation) | 0.02 |
| dl-α-Tocopherol acetate | 0.05 |
| Isostearyl glycyrrhetinate | 0.1 |
| Isopropylmethylphenol | 0.1 |
| Zinc white | 1.5 |
| Ethanol | 5.0 |
| Antiseptic | q.s. |
| Perfume base | q.s. |
| Purified water | Balance |
| Total | 100 |

Example 14: (Cosmetic emulsion)

A cosmetic emulsion was prepared in accordance with the following formulation.

| | (%) |
|---|---|
| Isostearyl 10-hydroxyundecanoate | 1.25 |
| Ethyl 9-hydroxyundecanoate | 0.46 |
| Glyceryl 8-hydroxyundecanoate | 0.09 |
| N-(3-hexadecyloxy-2-hydroxypropyl)-N-2-hydroxyethyldecanamide | 0.5 |
| N-(3-hexadecyloxy-2-hydroxypropyl)-N-2-hydroxyethylhexadecanamide | 1.0 |
| N-(3-tetradecyloxy-2-hydroxypropyl)-N-2-hydroxyethyldecanamide | 0.5 |
| Polyoxyethylene hardened castor oil (10 EO) | 1.0 |
| Methylpolysiloxane.methyl (polyoxyethylene)-siloxane copolymer (SH3773C, product of Dow Corning Toray Silicone Co., Ltd.) | 1.0 |
| Sorbitan monostearate | 0.2 |
| Sodium stearoylmethyltaurine | 0.5 |
| Cholesterol | 0.8 |
| Cholesterol isostearate | 0.2 |
| Monocholesteryl alkenylsuccinate | 0.8 |
| Stearic acid | 0.5 |
| Squalane | 4.0 |
| Methylpolysiloxane [KF96A-500cs, product of Shin-Etsu Chemical Co., Ltd.) | 2.0 |
| 2-Ethylhexyl p-methoxycinnamate (Parsol MCX-SA, product of Givaudan K.K.) | 2.0 |
| Cetyl alcohol | 1.0 |
| Glycerol | 3.5 |
| Lactic acid | 0.2 |
| Sodium lactate | 0.3 |
| Antiseptic | q.s. |
| Perfume base | q.s. |
| Purified water | Balance |
| Total | 100 |

Example 15: (Pack)

A pack was prepared in accordance with the following formulation.

| | (%) |
|---|---|
| 10-Hydroxyundecanoic acid | 4.0 |
| 9-Hydroxyundecanoic acid | 0.85 |
| 8-Hydroxyundecanoic acid | 0.15 |
| Polyvinyl alcohol (Gosenol EG-30, product of The Nippon Synthetic Chemical Industry Co., Ltd.) | 15.0 |
| Aqueous solution of carboxymethylchithin (Chithin Liquid HV-10, product of Ichimaru Pharcos Co., Ltd.) | 5.0 |
| Triglucopolysaccharide (Pullulan PL-20, product of Hayashibara Company, Ltd.) | 0.5 |
| Xanthan gum | 0.5 |
| Sodium carboxymethylcellulose | 0.5 |
| Titanium oxide | 15.0 |
| Aluminum magnesium silicate | 1.0 |
| 1-Isostearoyl-3-myristoyl-glycerol | 1.0 |
| Diglycerol | 1.5 |
| Polyoxyethylene isocetyl ether (20 EO) | 1.0 |
| Ethanol | 5.0 |
| Antiseptic | q.s. |
| Perfume base | q.s. |
| Purified water | Balance |
| Total | 100 |

Example 16: (Pack)

A pack was prepared in accordance with the following formulation.

| | (%) |
|---|---|
| 10-Hydroxyundecanoic acid | 4.0 |
| 10-Hydroxydodecanoic acid | 0.85 |
| 7-Hydroxydecanoic acid | 0.15 |
| Polyvinyl alcohol (Gosenol EG-30, product of The Nippon Synthetic Chemical Industry Co., Ltd.) | 15.0 |
| Aqueous solution of carboxymethylchithin (Chithin Liquid HV-10, product of Ichimaru Pharcos Co., Ltd.) | 5.0 |
| Triglucopolysaccharide (Pullulan PL-20, product of Hayashibara Company, Ltd.) | 0.5 |
| Xanthan gum | 0.5 |
| Sodium carboxymethylcellulose | 0.5 |
| Titanium oxide | 15.0 |
| Aluminum magnesium silicate | 1.0 |
| 1-Isostearoyl-3-myristoyl-glycerol | 1.0 |
| Diglycerol | 1.5 |
| Polyoxyethylene isocetyl ether (20 EO) | 1.0 |
| Ethanol | 5.0 |
| Antiseptic | q.s. |
| Perfume base | q.s. |
| Purified water | Balance |
| Total | 100 |

This application is based on Japanese Patent Application No. 7-88283, filed on Apr. 13, 1995, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters Patent of the United States is:

1. An external skin-care composition, comprising:
   (a) a hydroxycarboxylic acid or a derivative thereof represented by the following general formula (1) or a salt thereof;
   (b) a hydroxycarboxylic acid or a derivative thereof represented by the following general formula (2) or a salt thereof; and
   (c) a hydroxycarboxylic acid or a derivative thereof represented by the following general formula (3) or a salt thereof:

$$CH_3CH(CH_2)_l\overset{\overset{OH}{|}}{C}OR^1 \quad (1)$$

$$CH_3CH_2CH(CH_2)_m\overset{\overset{OH}{|}}{C}OR^2 \quad (2)$$

$$CH_3CH_2CH_2CH(CH_2)_n\overset{\overset{OH}{|}}{C}OR^3 \quad (3)$$

wherein $R^1$, $R^2$, and $R^3$ are each independently a hydroxyl group, an amino group or an alkoxyl group which may be substituted by 1–3 hydroxyl groups, l is a number of 7–11, m is a number of 6–10, and, wherein when l is a number equal to x, m is a number equal to x−1 and n is a number equal to x−2.

2. The composition of claim 1, wherein in general formula (1), l is 8, in the general formula (2), m is 7, and in the general formula (3), n is 6.

3. The composition of claim 1, wherein in general formulae (1), (2), and (3), $R^1$, $R^2$, and $R^3$ are hydroxyl groups.

4. The composition of claim 1, wherein said hydroxycarboxylic acids or derivatives thereof represented by the general formulae (1), (2), and (3), or the salts thereof are present in a ratio (1):(2):(3) of 60–95:4–35:1–5, by weight.

5. The composition of claim 1, wherein said hydroxycarboxylic acids or derivatives thereof represented by the general formulae (1), (2), and (3), or the salts thereof are present in an amount of 0.001–50 wt. %, based on the total weight of said composition.

6. The composition of claim 1, wherein said composition is a cosmetic skin-care composition.

7. The composition of claim 1, wherein said composition is a cosmetic skin-care composition of an emulsified type.

8. The composition of claim 1, wherein in general formulae (1), (2), and (3), $R^1$, $R^2$, and $R^3$ are hydroxy groups, l is 8, m is 7, and n is 6.

9. A method for treating or preventing skin roughness, said method comprising applying to skin a cosmetic composition, said cosmetic composition comprising:

(a) a hydroxycarboxylic acid or a derivative thereof represented by the following general formula (1) or a salt thereof;

(b) a hydroxycarboxylic acid or a derivative thereof represented by the following general formula (2) or a salt thereof; and (c) a hydroxycarboxylic acid or a derivative thereof represented by the following general formula (3) or a salt thereof:

(1)

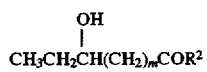

(2)

(3)

wherein $R^1$, $R^2$, and $R^3$ are each independently a hydroxyl group, an amino group or an alkoxyl group which may be substituted by 1–3 hydroxyl groups, l is a number of 7–11, m is a number of 6–10, and n is a number of 5–9.

10. The method of claim 9, wherein in general formula (1), l is 8, in the general formula (2), m is 7, and in the general formula (3), n is 6.

11. The method of claim 9, wherein in general formulae (1), (2), and (3), $R^1$, $R^2$, and $R^3$ are hydroxyl groups.

12. The method of claim 9, wherein said hydroxycarboxylic acids or derivatives thereof represented by the general formulae (1), (2), and (3), or the salts thereof are present in a ratio (1):(2):(3) of 60–95:4–35:1–5, by weight.

13. The method of claim 9, wherein said hydroxycarboxylic acids or derivatives thereof represented by the general formulae (1), (2), and (3), or the salts thereof are present in an amount of 0.001–50 wt. %, based on the total weight of said composition.

14. The method of claim 9, wherein said composition is a cosmetic skin-care composition.

15. The method of claim 9, wherein said composition is a cosmetic skin-care composition of an emulsified type.

16. The method of claim 9, wherein in general formulae (1), (2), and (3), $R^1$, $R^2$, and $R^3$ are hydroxy groups, l is 8, m is 7, and n is 6.

17. A method for making skin tone clear or reducing skin dullness, said method comprising applying to skin a cosmetic composition, said cosmetic composition comprising:

(a) a hydroxycarboxylic acid or a derivative thereof represented by the following general formula (1) or a salt thereof;

(b) a hydroxycarboxylic acid or a derivative thereof represented by the following general formula (2) or a salt thereof; and (c) a hydroxycarboxylic acid or a derivative thereof represented by the following general formula (3) or a salt thereof:

(1)

(2)

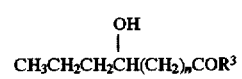

(3)

wherein $R^1$, $R^2$, and $R^3$ are each independently a hydroxyl group, an amino group or an alkoxyl group which may be substituted by 1–3 hydroxyl groups, l is a number of 7–11, m is a number of 6–10, and n is a number of 5–9.

18. The method of claim 17, wherein in general formula (1), l is 8, in the general formula (2), m is 7, and in the general formula (3), n is 6.

19. The method of claim 17, wherein in general formulae (1), (2), and (3), $R^1$, $R^2$, and $R^3$ are hydroxyl groups.

20. The method of claim 17, wherein said hydroxycarboxylic acids or derivatives thereof represented by the general formulae (1), (2), and (3), or the salts thereof are present in a ratio (1):(2):(3) of 60–95:4–35:1–5, by weight.

* * * * *

UNITED STATES PATENT AND TRADEMARK OFFICE
CERTIFICATE OF CORRECTION

PATENT NO. : 5,783,601
DATED : JULY 21, 1998
INVENTOR(S) : MASANORI TANAHASHI, ET AL

It is certified that error appears in the above-identified patent and that said Letters Patent is hereby corrected as shown below:

Column 18, line 56 "6-10, and," should read --6-10, and n is a number of 5-9,--

Signed and Sealed this

Second Day of February, 1999

Attest:

Attesting Officer

*Acting Commissioner of Patents and Trademarks*